United States Patent
Majeed et al.

(10) Patent No.: US 8,853,407 B1
(45) Date of Patent: Oct. 7, 2014

(54) SYNTHESIS OF 4-ARYL 4-ACYL PIPERIDINE, ITS SALTS AND ANALOGS USING INDIUM METAL

(71) Applicants: Muhammed Majeed, Edison, NJ (US); Rajendran Ramanujam, Bangalore (IN); Kalyanam Nagabhushanam, East Windsor, NJ (US)

(72) Inventors: Muhammed Majeed, Edison, NJ (US); Rajendran Ramanujam, Bangalore (IN); Kalyanam Nagabhushanam, East Windsor, NJ (US)

( * ) Notice: Subject to any disclaimer, the term of this patent is extended or adjusted under 35 U.S.C. 154(b) by 0 days.

(21) Appl. No.: 14/099,913

(22) Filed: Dec. 7, 2013

(51) Int. Cl.
  *C07D 211/82* (2006.01)
  *C07D 211/32* (2006.01)

(52) U.S. Cl.
  CPC ............ *C07D 211/32* (2013.01); *C07D 211/82* (2013.01)
  USPC ........................................................ 546/185

(58) Field of Classification Search
  None
  See application file for complete search history.

(56) References Cited

PUBLICATIONS

Atlani et al., 1,4,-diacyl-4-alkyldihydropyridines, 29(2) Tetrahedron 391-8 (1973).*

* cited by examiner

*Primary Examiner* — Janet L Andres
*Assistant Examiner* — Timothy R Rozof (57) ABSTRACT

A novel process for the synthesis of 4-aryl 4-acyl piperidine derivatives using indium metal is described. Specifically, a novel process for the synthesis of 4-acetyl 4-phenyl piperidine and its salts using indium metal is described.

7 Claims, 4 Drawing Sheets

FIG.1-Prior Art (1-benzyl 4-acetyl 4-phenyl piperidine)    (4-acetyl 4-phenyl piperidine)

FIG.4-ILLUSTRATIVE MECHANISM

SYNTHESIS OF 4-ARYL 4-ACYL PIPERIDINE, ITS SALTS AND ANALOGS USING INDIUM METAL

BACKGROUND OF THE INVENTION

1. Field of the Invention

The invention in general relates to the synthetic process for 4,4-Disubstituted piperidines. More specifically, the present invention relates to a novel process for the synthesis of 4-aryl 4-acyl piperidine derivatives using indium metal. Still more specifically, the present invention relates to a novel process for the synthesis of 4-acetyl 4-phenyl piperidine and its salts using indium metal.

2. Description of Prior Art

Disubstituted piperidines have been a part of many investigational drug molecules (Wieslaw M. Kazmierski et. al., *Journal of Medicinal Chemistry*, 2011, 54, 3756). Representative example 4-acetyl 4-phenyl piperidine and its derivatives are extensively discussed in (Wieslaw M. Kazmierski et. al., *Journal of Medicinal Chemistry*, 2008, 51, 6538).

The biological properties and applications of 4-Acetyl-4-phenyl piperidine have been reported in prior art.

a. 4-Acetyl 4-phenyl piperidine as a novel chlorokojic acid derivative has been investigated for its cytotoxicity along with its antimicrobial and antiviral activities (MutluDilsizAytemir, BerrinOzcelik, *European Journal of Medicinal Chemistry*, 2010, 45, 4089).

b. Several derivatives of 4-acetyl 4-phenyl piperidine were synthesized and evaluated for analgesic activity by Z. S. Saify et al., *ZeitschriftfuerNaturforschung, B: Chemical Sciences*; vol. 54; nb. 10; (1999); p. 1327-1336.

c. 4-acetyl 4-phenyl piperidine has been part of the design and synthesis of Novel $\alpha_{1a}$adrenoceptor-selective dihydropyridine antagonists beneficial in the treatment of benign prostatic hyperplasia (DhanapalanNagarathnam et. al., *Journal of Medicinal Chemistry*, 1998, 41, 5320).

In spite of such extensive applications of 4-acetyl 4-phenyl piperidine in the fields of investigation drugs and medicinal chemistry, the synthesis of 4-acetyl 4-phenyl piperidine has not been easy. Prior art synthetic schemes as disclosed herein below are fret with technical problems including very long and arduous synthetic schemes, use of hazardous chemical agents for synthesis, non-feasible reaction conditions and non-scalability of process inventions at the industrial level.

For example, 4-acetyl 4-phenyl piperidine has been made from its N-benzyl derivative by hydrogenation using palladium/hydrogen for debenzylation (*Journal of Organic Chemistry*; vol. 22; (1957); p. 1484, 1488) [FIG. 1—Prior Art].

The starting material, 1-benzyl 4-acetyl 4-phenyl piperidine has been synthesized from 1-benzyl 4-cyano 4-phenyl piperidine using methyl magnesium bromide in toluene/THF medium. (Teraoka, Takashi and Uno, Osamu, *Jpn. KokaiTokkyoKoho*, 2007119406) and using methyl lithium (Perrine, T. D., *Journal of Organic Chemistry*, 1957, 22, 1484) [FIG. 2-Prior Art].

Further, 1-benzyl 4-cyano 4-phenyl piperidine has been synthesized from

1. Phenyl acetonitrile and N-benzyl 2-chloro(2-chloroethyl)ethanamine using sodium hydroxide as base under PTC catalysis (Leng, Xiansheng et al., *From Faming ZhuanliShenqingGongkaiShuomingshu*, 1535967, 13 Oct. 2004.

2. Benzylamine and 4-hydroxy-2-(2-hydroxyethyl)-2-phenylbutanenitrile (Asano, Shigehiro and Ban, Hitoshi, *Heterocycles*, 75(1), 183-188; 2008).

3. Phenyl acetonitrile and N-benzyl 2-chloro(2-chloroethyl)ethanamine using sodamide in toluene (Pajouhesh, Hassan et al., PCT Int. Appl., 2008031227, 20 Mar. 2008).

4. Phenyl acetonitrile and N-benzyl 2-chloro(2-chloroethyl)ethanamine using sodium hydride in THF at 80 degrees (Tang, Haifeng et al., *Bioorganic & Medicinal Chemistry Letters*, 20(20), 6088-6092; 2010)

Figure 3:
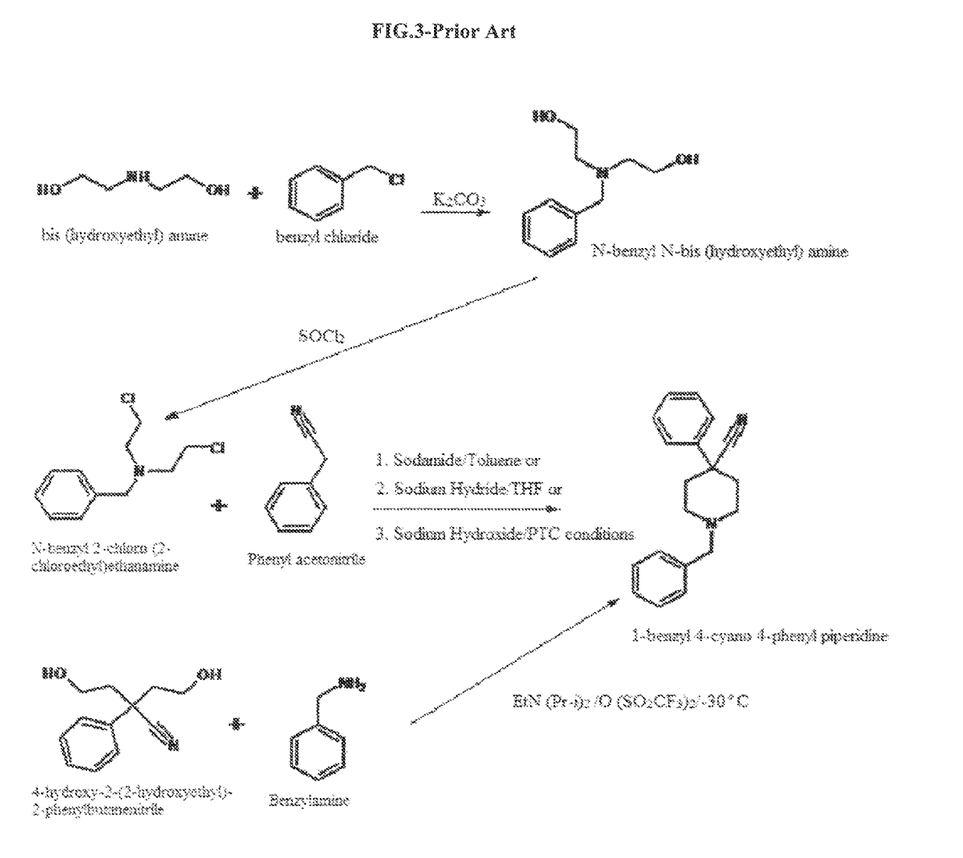
FIG. 3—Prior Art represents the synthetic schemes for 1-benzyl 4-cyano 4-phenyl piperidine.

Schematically presented in FIG. 3—Prior Art.

Figure 1:
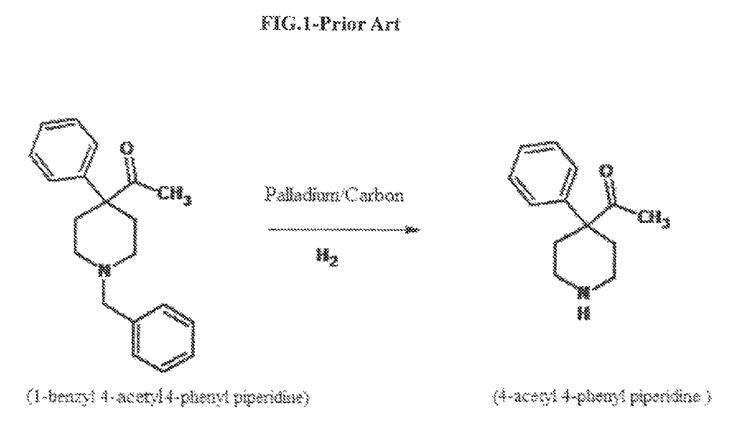
FIG. 1—Prior Art represents the synthetic scheme for 4-acetyl 4-phenyl piperidine.
Figure 2:
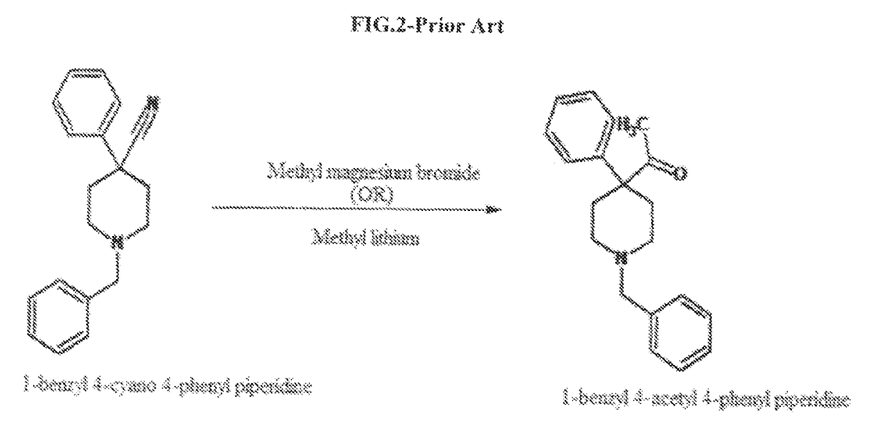
FIG. 2—Prior Art represents the synthetic scheme for 1-benzyl 4-acetyl 4-phenyl piperidine.

It is clear that the synthetic schemes represented in FIGS. 1, 2 and 3—Prior Art have several process steps, use hazardous chemicals like sodium hydride, sodamide, triflic anhydride, include non-feasible reaction conditions like very low temperature conditions (−30° C.) making industrial applicability and scalability difficult. Thus, there is a need for practical, safe, scalable synthetic method for the synthesis of 4-acetyl 4-phenyl piperidine or in general the 4-aryl 1,4-diacyl dihydropyridine group of compounds.

It is thus the principle objective of the present invention to disclose shorter synthetic scheme for 4-acetyl 4-phenyl piperidine, the steps of which are easy to adopt, do not use hazardous chemicals and unfavorable reaction conditions and are industrially scalable to produce considerable quantities of 4-acetyl 4-phenyl piperidine.

The principle objective mentioned herein above in general also encompasses the synthetic scheme for 4-aryl 4-acyl piperidine derivatives using indium metal.

The present invention fulfills the aforesaid objectives and provides further related advantages.

SUMMARY OF THE PRESENT INVENTION

The present invention relates to a novel process for the synthesis of 4-aryl 4-acyl piperidine derivatives using indium metal. Still more specifically the present invention relates to a novel process for the synthesis of 4-acetyl 4-phenyl piperidine and its salts using indium metal.

The advantages of the present invention are as follows.

A. Starting material 4-phenylpyridine for the synthetic scheme of the instant innovation is commercially available in bulk quantities or can be easily prepared by various published methods known in the literature. 4 phenyl pyridine is easily made either by reacting phenyl boronic acid with 4 halo pyridines (Moseley Jonathan D et al, *Tetrahedron*, 2012, 68 (30), 6010 and Edkins, Robert M et al, *Dalton Transactions*, 2011, 40 (38), 9672) or by reacting halobenzenes with 4-pyridine boronic acid (Xu Chen et al; *Transition Metal Chemistry* (Dordrecht, Netherlands), 2012, 37, 4, 373 and Kudo Noriaki et al; *Angewandte Chemie, International Edition*, 2006, 45, 8, 1282).

B. The use of indium metal confers specific advantages over other metals used in art like zinc used in prior art (P. M. Atlani et al. *Tetrahedron*, 1973, 29, 391) namely, a. The first ionization potential of indium metal (In) (5.8 eV) is as low as that of Li and Na. Therefore, it might be easy for In to promote SET (single electron transfer) processes.

b. Metallic indium is comparatively stable in air, and the toxicity observed in many metals is little known in metallic indium.

c. Indium used in the instant invention can be a powder, or in the form of flakes or in the form of a wire or as nanoparticles. Generally powder or wire is used. These different physical forms of indium have the same chemical property in reductively acylating the pyridine nucleus as described in this invention.

d. Metals like zinc used in prior art led to moderate conversions with poor yields.

Other features and advantages of the present invention will become apparent from the following more detailed descrip-

DETAILED DESCRIPTION OF THE FIGURES

DETAILED DESCRIPTION OF THE INVENTION

In the most preferred embodiment (first embodiment) the present invention relates to a novel synthetic scheme for 4,4-Disubstituted piperidines. More specifically, the present invention relates to a novel process for the manufacture of 4-aryl 1,4-diacyl 1,4-dihydropyridine of the general structure I (STR#1) comprising the steps of

(a) Mixing 4-arylpyridine, acid anhydride and indium metal in a reactor;
(b) Raising the reaction temperature to about 50°-110° C.;
(c) Maintaining the reaction time ranging from 1 hr to 24 hrs;
(d) Quenching the reaction with water and
(e) Isolating the final product 4-aryl 1,4-diacyl 1,4-dihydropyridine by crystallization or chromatography.

STR#I

In a preferred embodiment, the Ar⁻ functional group of STR#1 is selected from the group consisting of phenyl, alkyl phenyl, aryl phenyl, naphthyl and aryl alkyl. In another preferred embodiment the R functional group of STR#1 is selected from methyl, ethyl, propyl, butyryl, t-butyl, phenyl and benzyl. In yet another preferred embodiment, the indium metal used in the aforesaid process step is selected from its physical forms of powder, nanopowder, sheets and wire.

In another most preferred embodiment, the present invention relates to a novel synthetic process for 4-aryl 1,4-diacyl piperidine of the general structure II (STR#II) comprising the steps of reduction of 4-aryl 1,4-diacyl 1,4-dihydropyridine of STR#1.

STR#II

In a preferred embodiment, said steps of reduction are mediated by agents selected from group consisting of palladium/hydrogen, platinum/hydrogen and nickel/hydrogen.

In yet another most preferred embodiment, the present invention also relates to a novel synthetic process for 4-aryl 4-acyl piperidine of the general structure III (STR#III) comprising the steps of hydrolysis of 4-aryl 1,4-diacyl piperidine of general structure II (STR#II) with metal hydroxides.

STR#III

In a specific embodiment, the metal hydroxides are selected from group consisting of sodium hydroxide, potassium hydroxide and barium hydroxide.

In yet another most preferred embodiment, the present invention relates to a chemical compound represented by STR#II.

STR#II

In a preferred embodiment, the Ar⁻ functional group of STR#II is selected from the group consisting of phenyl, alkyl phenyl, aryl phenyl, naphthyl and aryl alkyl.

In yet another most preferred embodiment, the present invention also relates to a novel process for the synthesis of 4-acetyl 4-phenyl piperidine and its salts using indium metal, said process comprising the steps of A. Acylation of 4-phenyl pyridine using acid anhydride in the presence of indium to get 1,4 diacetyl 4-phenyl 1,4 dihydropyridine (Equation A);

(Equation A)

4-phenyl pyridine 1,4 diacetyl 4-phenyl 1,4 dihydropyridine

B. Reduction of 1,4 diacetyl 4-phenyl 1,4 dihydropyridine using homogenous or heterogenous hydrogenation systems to get 1,4 diacetyl 4-phenyl piperidine (Equation B);

(Equation B)

1,4-diacetyl 4-phenyl 1,4-dihydropyridine → 1,4-diacetyl 4-phenyl piperidine (STR#IV)

C. Hydrolysis of 1,4 diacetyl 4-phenyl piperidine using metal hydroxides to get the target product 4-acetyl 4-phenyl piperidine as its hydrochloride salt (Equation C).

(Equation C)

1,4 diacetyl 4-phenyl piperidine → Hydrochloride salt of 4-acetyl 4-phenyl piperidine In yet another preferred embodiment, the present invention also relates to the chemical compound represented by STR#IV.

(STR#IV)

Figure 4:
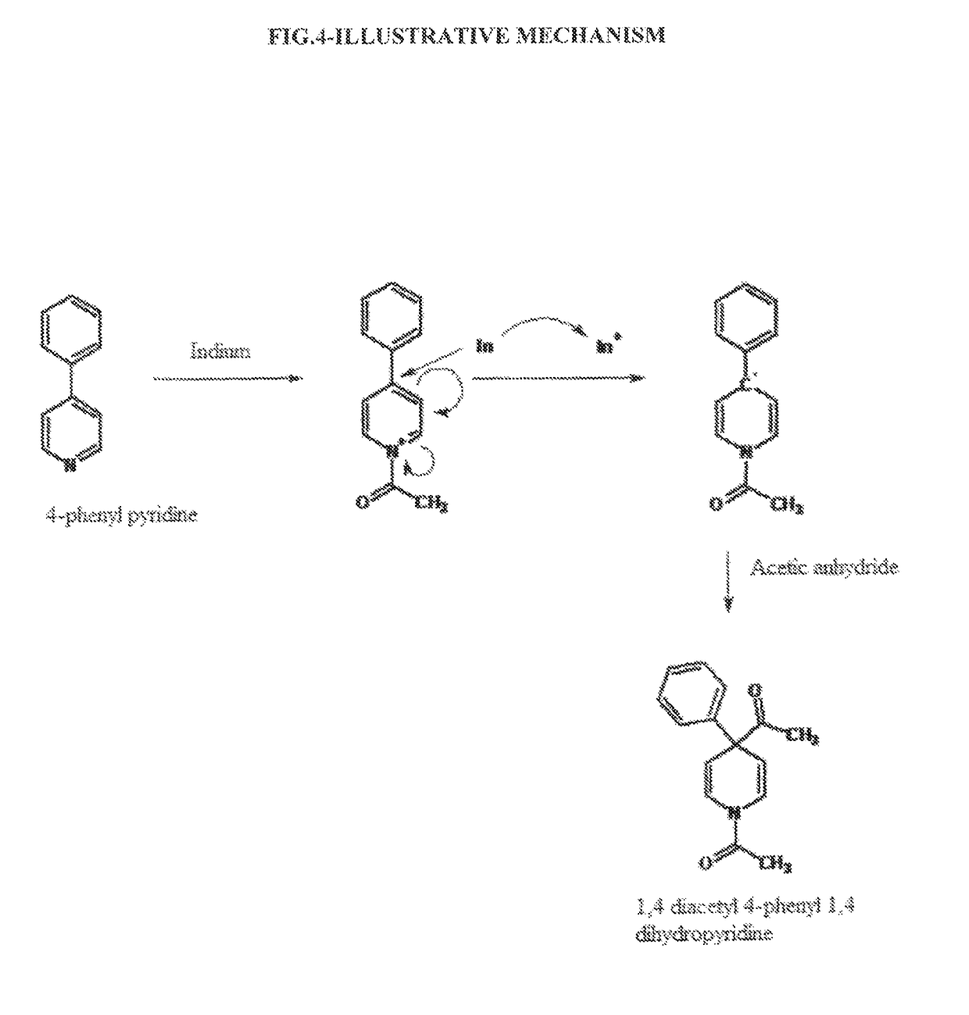
FIG. 4 represents the illustrative mechanism underlying the acylation of 4-phenyl pyridine using acid anhydride in the presence of indium to get 1,4 diacetyl 4-phenyl 1,4 dihydropyridine (Equation A)

As an insight into the speculative mechanism of Equation A, the present inventors illustrate the same in FIG. 4.

The underlying sections of this specification provided illustrative examples for the synthetic processes and compounds thereof discussed herein above.

Example 1

Synthesis of 1,4-diacetyl 4-phenyl 1,4-dihydropyridine 1 gram of 4-phenyl pyridine was taken in 6 ml of acetic anhydride and 1 g of indium powder was added under stirring. The mixture was heated slowly over a period of 1 hr to 95-100° C. The reaction mixture was maintained at 95-100° C. for 6 hrs when the thin layer chromatography showed the completion of the reaction.

The mixture was cooled to ambient temperature and 10 ml water was added and stirred further for 1 hour. 25 ml of ethyl acetate was added and filtered to remove the indium metal.

The organic layer was separated and washed with sodium bicarbonate solution followed by water and brine solution. The organic layer was dried over sodium sulphate and concentrated to get the crude product which was subjected to column chromatography and eluted with chloroform. The pure solid product of 1,4-diacetyl 4-phenyl 1,4-dihydropyridine was obtained by precipitation with hexane.

Yield: 1.2 g

Melting point: 93-95° C.

1H NMR (300 MHz, CDCl$_3$) δ (PPM) 7.44-7.50 (d, 1H), 7.16-7.7.42 (m, 5H), 6.72-6.80 (d, 1H), 5.36-5.44 (dd, 1H), 5.22-5.30 (dd, 1H), 2.24-2.26 (s, 3H), 2.05-2.07 (s, 3H)

13C NMR (300 MHz, CDCl$_3$) δ (PPM) 206.65, 166.57, 143.31, 129.44, 127.57, 126.67, 123.11, 122.54, 109.29, 108.15, 57.32, 25.54, 21.53

The above procedure was applied for 4-substituted phenyl pyridines like methoxy phenyl, chlorophenyl, alkylphenyl etc., and the products were obtained after purification by column chromatography.

Reactions were done using propionic anhydride, butyric anhydride, isobutyric anhydride, benzoic anhydride etc., in place of acetic anhydride and the products were obtained after purification by column chromatography.

Example 2

Synthesis of 1,4 diacetyl 4-phenyl piperidine (STR#II)

1.2 grams of 1,4-Diacetyl 4-phenyl 1,4-dihydropyridine from Example 1 was dissolved in methanol (100 ml) and subjected to hydrogenation in an autoclave in presence of Palladium/carbon (10%) at 60° C. with hydrogen pressure of 5-6 kg for 10 hrs. Thin layer chromatography showed the completion of the reduction. The reaction mixture was cooled to room temperature and filtered to remove palladium/carbon. The filtrate was concentrated completely and the product was precipitated using chilled isopropyl alcohol. The product was filtered and the solid product 1,4 diacetyl 4-phenyl piperidine was dried under vacuum.

Yield: 1 g

Melting point: 66-68° C.

1H NMR (300 MHz, CDCl$_3$) δ (PPM) 7.20-7.35 (m, 5H), 4.10-4.30 (dt, 1H), 3.30-3.70 (m, 2H), 3.00-3.20 (t, 1H), 2.30-2.60 (dd, 2H), 1.80-2.20 (m, 2H), 1.93 (s, 3H), 2.08 (s, 3H)

13C NMR (300 MHz, CDCl$_3$) δ (PPM) 209.08, 169.17, 140.83, 129.39, 127.81, 126.43, 55.06, 44.01, 38.93, 33.93, 31.86, 25.75, 21.55

Example 3

Synthesis of 4-acetyl 4-phenyl piperidine hydrochloride

1 gram of 1,4 diacetyl-4-phenyl piperidine obtained in Example 2 was dissolved in 25 ml of methanol and sodium hydroxide solution (500 mg dissolved in 2.5 ml water) was added at room temperature. The solution was stirred at ambient temperature for 10 hrs. Thin layer chromatography showed the complete hydrolysis. The pH of the reaction mixture was adjusted to 2 using dilute hydrochloric acid and filtered to remove the salts. The filtrate was concentrated to remove methanol completely. 25 ml of isopropyl alcohol was added to precipitate the target molecule 4-acetyl 4-phenyl piperidine hydrochloride as white crystalline product. The product was dried under vacuum at 60° C.

Yield: 800 mg
Melting point: 234-236° C.
1H NMR (300 MHz, DMSO) δ (PPM) 9.10-9.20 (bs, 2H), 7.30-7.50 (m, 5H), 2.80-3.20 (m, 4H), 2.40-2.60 (dt, 2H), 2.10-2.30 (m, 2H), 1.913 (s, 3H)
13C NMR (300 MHz, CDCl$_3$) δ (PPM) 208.78, 140.33, 129.88, 128.32, 126.96, 53.57, 41.28, 40.98, 39.32, 29.02, 25.82

Example 4

Synthesis of 1,4-dibutyryl 4-phenyl 1,4-dihydropyridine

1 gram of 4-Phenyl pyridine was taken in 6 ml of n-butyric anhydride and 1 gram of indium powder was added under stirring. The mixture was heated slowly over a period of 1 hr to 95-100° C. The reaction mixture was maintained at 95-100° C. for 6 hrs when the thin layer chromatography showed the formation of the product with the starting material still present. The mixture was cooled to ambient temperature and 10 ml of water was added and stirred further for 1 hour. 25 ml of ethyl acetate was added and filtered to remove the indium metal. The organic layer was separated and washed with sodium bicarbonate solution followed by water and brine solution. The organic layer was dried over sodium sulphate and concentrated to get the crude product which was subjected to column chromatography and eluted with chloroform to obtain the product 1,4-dibutyryl 4-phenyl 1,4-dihydropyridine as a thick colorless liquid.

1, 4-dibutyryl 4-phenyl
1, 4-dihydropyridine

Yield: 750 mg
1H NMR (300 MHz, CDCl$_3$) δ (PPM) 7.45-7.55 (d, 1H), 7.35-7.44 (t, 2H), 7.15-7.30 (m, 3H), 6.75-6.85 (d, 1H), 5.25-5.35 (d, 1H), 5.35-5.45 (d, 1H), 2.40-2.50 (t, 2H), 2.30-2.40 (q, 2H), 1.66-1.80 (m, 2H), 1.50-1.64 (m, 2H), 0.94-1.06 (t, 3H), 0.78-0.88 (t, 3H)
13C NMR (300 MHz, CDCl$_3$) δ (PPM) 209.07, 169.11, 143.56, 129.36, 127.45, 126.74, 122.64, 122.43, 109.34, 108.13, 57.05, 39.77, 35.27, 18.19, 17.75, 14.03, 13.89

The product 1,4-dibutyryl 4-phenyl 1,4-dihydropyridine was hydrogenated as detailed in Example 2 and further hydrolyzed as detailed in Example 3 to furnish the final product 4-phenyl 4-butyryl piperidine.

4-phenyl
4-butyryl piperidine

CONCLUSION, RAMIFICATION AND SCOPE

While the above description contains many specificities, these should not be construed as limitations on the scope of any embodiment, but as exemplifications of the presently preferred embodiments. Many other ramifications and variations are possible within the teachings of the various embodiments. For example, even though the sequence disclosed above uses 4-phenylpyridine as an example, the scope of the invention is not limited to 4-phenyl pyridine as the starting material. The starting material for Equation A may in general be a 4-aryl pyridine. For example, if 4-(p-methyl-phenyl) pyridine be a starting material, this will ultimately lead to, by the synthetic sequence described, 4-(p-methyl-phenyl)-4-acetyl piperidine as the final product either as the free base or as a salt depending on the method of isolation. The hydrolysis (Equation C) can be done using metal hydroxides such as sodium hydroxide or potassium hydroxide. The practitioners of art will immediately recognize that other bases such lithium, calcium or other metal hydroxides could be used in addition to use of quarternary ammonium hydroxides and salts as phase transfer agents. Such variations are also covered under this invention. Also the acylating agent described in Equation A is not limited to acetic anhydride. Any acid anhydride could be used. Similarly the reduction (Equation B) is carried out by hydrogenation using palladium. Other hydrogenation methods could be adopted. Instead of heterogenous hydrogenation like the Palladium on carbon hydrogenation, homogenous hydrogenation could also be used. Among the heterogenous hydrogenation platinum/hydrogen or Raney nickel/hydrogen are possible variations. Homogenous catalysis using triphenylphosphine rhodium chloride/hydrogen is also possible. Thus the invention provides a convenient route to a diversely substituted 4-aryl 4-acyl piperidine either as the base or as a salt such as hydrochloride salt of the general structure III (STR#III) discussed in the specification. Other salts such as sulphate or salts of organic acids such as acetate, succinate, maleate are possible and such variations of this invention are also covered in this application.

We claim:

1. A process for the manufacture of 4-aryl 1,4-diacyl 1,4-dihydropyridine of the general structure I (STR#1) comprising the steps of
   a. Mixing 4-arylpyridine, acid anhydride and indium metal in a reactor
   b. Raising the reaction temperature to about 50°-110° C.
   c. Maintaining the reaction time ranging from 1 hr to 24 hrs
   d. Quenching the reaction with water and
   e. Isolating the final product 4-aryl 1,4-diacyl 1,4-dihydropyridine by crystallization or chromatography

STR#I

Wherein the Ar⁻ functional group is selected from the group consisting of phenyl, alkyl phenyl, aryl phenyl, naphthyl and aryl alkyl, and
The R functional group is selected from methyl, ethyl, propyl, butyl, t-butyl, phenyl and benzyl.

2. The process of claim 1 wherein the indium metal used is selected from the group of its physical forms consisting of powder, nanopowder, sheets and wire.

3. A synthetic process for 4-aryl 1,4-diacyl piperidine of the general structure II (STR#II) comprising the steps of reduction of 4-aryl 1,4-diacyl 1,4-dihydropyridine of STR#1

(STR#I)

(STR#II)

Wherein the Ar⁻ functional group is selected from the group consisting of phenyl, alkyl phenyl, aryl phenyl, naphthyl and aryl alkyl, and
The R functional group is selected from methyl, ethyl, propyl, butyl, t-butyl, phenyl and benzyl.

4. The process of claim 3 wherein said steps of reduction are mediated by systems selected from group consisting of palladium/hydrogen, platinum/hydrogen and nickel/hydrogen.

5. A process for the synthesis of 4-acetyl 4-phenyl piperidine and its salts using indium metal, said process comprising the steps of
   A. Acylation of 4-phenyl pyridine using acid anhydride in the presence of indium to get 1,4 diacetyl 4-phenyl 1,4 dihydropyridine (Equation A);

(Equation A)

4-phenyl pyridine 1,4 diacetyl 4-phenyl 1,4 dihydropyridine

B. Reduction of 1,4 diacetyl 4-phenyl 1,4 dihydropyridine using homogenous or heterogenous hydrogenation systems to get 1,4 diacetyl 4-phenyl piperidine (Equation B);

(Equation B)

1,4 diacetyl 4-phenyl 1,4 dihydropyridine 1,4-diacetyl 4-phenyl piperidine (STR#IV)

C. Hydrolysis of 1,4 diacetyl 4-phenyl piperidine using suitable metal hydroxides to get the target product 4-acetyl 4-phenyl piperidine as its hydrochloride salt (Equation C)

(Equation C)

1,4 diacetyl 4-phenyl piperidine

Hydrochloride salt of 4-acetyl 4-phenyl piperidine

6. The process of claim 5 wherein the heterogeneous hydrogenation system is selected from the group consisting of palladium/carbon, platinum/hydrogen and Raney nickel/hydrogen.

7. The process of claim 5 wherein the homogenous hydrogenation system is triphenylphosphine rhodium chloride/hydrogen.

* * * * *